United States Patent
Morichika et al.

(10) Patent No.: US 11,767,363 B2
(45) Date of Patent: *Sep. 26, 2023

(54) HIGH CONCENTRATION ANTIBODY-CONTAINING LIQUID FORMULATION

(71) Applicants: CHUGAI SEIYAKU KABUSHIKI KAISHA, Tokyo (JP); HOFFMANN-LA ROCHE INC., Little Falls, NJ (US)

(72) Inventors: Toshiyuki Morichika, Tokyo (JP); Daisuke Kameoka, Tokyo (JP); Yoshimi Imaeda, Tokyo (JP); Terutoshi Maeda, Tokyo (JP); Oliver Boris Stauch, Freiburg (DE)

(73) Assignees: CHUGAI SEIYAKU KABUSHIKI KAISHA, Tokyo (JP); HOFFMANN-LA ROCHE INC., Little Falls, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 18/162,368

(22) Filed: Jan. 31, 2023

(65) Prior Publication Data

US 2023/0167183 A1  Jun. 1, 2023

Related U.S. Application Data

(60) Division of application No. 17/752,978, filed on May 25, 2022, now Pat. No. 11,584,798, which is a continuation of application No. 17/242,199, filed on Apr. 27, 2021, now Pat. No. 11,359,026, which is a continuation of application No. 16/390,197, filed on Apr. 22, 2019, now Pat. No. 11,008,394, which is a division of application No. 14/963,414, filed on Dec. 9, 2015, now abandoned, which is a division of application No. 14/017,013, filed on Sep. 3, 2013, now abandoned, which is a division of application No. 12/810,938, filed as application No. PCT/JP2008/073798 on Dec. 26, 2008, now Pat. No. 8,568,720.

(30) Foreign Application Priority Data

Dec. 27, 2007 (JP) .................. 2007-336310

(51) Int. Cl.
| | |
|---|---|
| A61K 39/395 | (2006.01) |
| C07K 16/28 | (2006.01) |
| A61K 47/18 | (2017.01) |
| A61K 47/26 | (2006.01) |
| C07K 1/14 | (2006.01) |
| A61K 47/20 | (2006.01) |
| A61K 9/00 | (2006.01) |
| A61K 39/00 | (2006.01) |

(52) U.S. Cl.
CPC ...... *C07K 16/2866* (2013.01); *A61K 39/3955* (2013.01); *A61K 39/39591* (2013.01); *A61K 47/183* (2013.01); *A61K 47/20* (2013.01); *A61K 47/26* (2013.01); *C07K 1/14* (2013.01); *A61K 9/0019* (2013.01); *A61K 2039/505* (2013.01); *C07K 2317/24* (2013.01); *C07K 2317/76* (2013.01)

(58) Field of Classification Search
CPC .................................................. A61K 39/395
See application file for complete search history.

(56) References Cited

U.S. PATENT DOCUMENTS

| | | |
|---|---|---|
| 5,171,840 A | 12/1992 | Kishimoto |
| 5,480,796 A | 1/1996 | Kishimoto |
| 5,670,373 A | 9/1997 | Kishimoto |
| 5,795,965 A | 8/1998 | Tsuchiya et al. |
| 5,817,790 A | 10/1998 | Tsuchiya et al. |
| 5,851,793 A | 12/1998 | Kishimoto |
| 5,888,510 A | 3/1999 | Kishimoto et al. |
| 5,990,282 A | 11/1999 | Kishimoto |
| 6,086,874 A | 7/2000 | Yoshida et al. |
| 6,261,560 B1 | 7/2001 | Tsujinaka et al. |
| 6,406,909 B1 | 6/2002 | Shibuya et al. |
| 6,410,691 B1 | 6/2002 | Kishimoto |

(Continued)

FOREIGN PATENT DOCUMENTS

| | | |
|---|---|---|
| CN | 1402640 A | 3/2003 |
| CN | 1798575 A | 7/2006 |

(Continued)

OTHER PUBLICATIONS

Request for Invalidation of Patent Rights filed with the China National Intellectual Property Administration on Oct. 31, 2019, against Chinese Patent No. 2008801190665, and accompanying reasons for invalidation, with English translations.

(Continued)

*Primary Examiner* — Prema M Mertz
(74) *Attorney, Agent, or Firm* — BROWDY AND NEIMARK, PLLC

(57) ABSTRACT

The problem to be solved is to provide a humanized anti-IL-6 receptor antibody AMA-containing formulation which is suitable for subcutaneous administration, wherein dimerization or deamidation is prevented during long-term storage. The present application is directed to a stable antibody-containing liquid formulation characterized by containing arginine and histidine buffer. A method of inhibiting deamidation or dimerization of such an antibody in a concentrated liquid formulation includes histidine buffer in the liquid formulation.

6 Claims, 4 Drawing Sheets

(56) References Cited

U.S. PATENT DOCUMENTS

| | | |
|---|---|---|
| 6,428,979 B1 | 8/2002 | Kishimoto |
| 6,537,782 B1 | 3/2003 | Shibuya et al. |
| 6,692,742 B1 | 2/2004 | Nakamura et al. |
| 6,723,319 B1 | 4/2004 | Ito et al. |
| 6,875,432 B2 | 4/2005 | Liu et al. |
| 6,908,610 B1 | 6/2005 | Sato |
| 6,962,812 B2 | 11/2005 | Shibuya et al. |
| 7,320,792 B2 | 1/2008 | Ito et al. |
| 7,332,289 B2 | 2/2008 | Takeda et al. |
| 7,479,543 B2 | 1/2009 | Tsuchiya et al. |
| 7,498,031 B2 | 3/2009 | Fujioka et al. |
| 7,521,052 B2 | 4/2009 | Okuda et al. |
| 7,566,453 B2 | 7/2009 | Nakamura et al. |
| 7,666,413 B2 | 2/2010 | Liu et al. |
| 7,771,723 B2 | 8/2010 | Nakamura et al. |
| 7,824,674 B2 | 11/2010 | Ito et al. |
| 7,927,815 B2 | 4/2011 | Takeda et al. |
| 7,955,598 B2 | 6/2011 | Yoshizaki et al. |
| 8,017,121 B2 | 9/2011 | Kishimoto et al. |
| 8,142,776 B2 | 3/2012 | Liu et al. |
| 8,173,126 B2 | 5/2012 | Yoshizaki et al. |
| 8,227,195 B2 | 7/2012 | Stubenrauch et al. |
| 8,398,980 B2 | 3/2013 | Kano et al. |
| 8,420,789 B2 | 4/2013 | Takeda et al. |
| 8,440,196 B1 | 5/2013 | Funakoshi et al. |
| 8,470,316 B2 | 6/2013 | Yasunami |
| 8,529,894 B2 | 9/2013 | Mihara et al. |
| 8,530,176 B2 | 9/2013 | Stubenrauch et al. |
| 8,562,990 B2 | 10/2013 | Ito et al. |
| 8,562,991 B2 | 10/2013 | Igawa et al. |
| 8,568,720 B2 | 10/2013 | Morichika et al. |
| 8,580,264 B2 | 11/2013 | Zhang et al. |
| 8,597,644 B2 | 12/2013 | Ito et al. |
| 8,617,550 B2 | 12/2013 | Nishimoto et al. |
| 8,623,355 B2 | 1/2014 | Okada et al. |
| 8,632,778 B2 | 1/2014 | Kakuta et al. |
| 8,703,126 B2 | 4/2014 | Liu et al. |
| 8,709,409 B2 | 4/2014 | Okuda et al. |
| 8,734,800 B2 | 5/2014 | Kano et al. |
| 8,771,686 B2 | 7/2014 | Ishida |
| 8,809,509 B2 | 8/2014 | Takeda et al. |
| 8,840,884 B2 | 9/2014 | Kakuta et al. |
| 8,921,527 B2 | 12/2014 | Mizushima et al. |
| 8,945,564 B2 | 2/2015 | Lu |
| 8,961,964 B2 | 2/2015 | Liu et al. |
| 9,051,384 B2 | 6/2015 | Kakuta et al. |
| 9,084,777 B2 | 7/2015 | Morichika et al. |
| 9,255,145 B2 | 2/2016 | Yoshizaki et al. |
| 9,539,263 B2 | 1/2017 | Zhang et al. |
| 9,630,988 B2 | 4/2017 | Lau et al. |
| 9,750,752 B2 | 9/2017 | Zhang et al. |
| 9,902,777 B2 | 2/2018 | Kano et al. |
| 10,022,319 B2 | 7/2018 | Igawa et al. |
| 10,166,293 B2 | 1/2019 | Liu et al. |
| 10,168,326 B2 | 1/2019 | Stubenrauch et al. |
| 10,231,981 B2 | 3/2019 | Zhang et al. |
| 10,316,096 B2 | 6/2019 | Morichika et al. |
| 10,349,940 B2 | 7/2019 | Zeiner et al. |
| 10,590,164 B2 | 3/2020 | Lau et al. |
| 10,744,201 B2 | 8/2020 | Okuda et al. |
| 10,961,314 B2 | 3/2021 | Del Rio et al. |
| 11,008,394 B2 | 5/2021 | Morichika et al. |
| 11,021,728 B2 | 6/2021 | Franze et al. |
| 2002/0045571 A1 | 4/2002 | Liu et al. |
| 2002/0187150 A1 | 12/2002 | Mihara et al. |
| 2003/0092622 A1 | 5/2003 | Sato et al. |
| 2003/0138417 A1 | 7/2003 | Kaisheva et al. |
| 2003/0180287 A1 | 9/2003 | Gombotz et al. |
| 2003/0190316 A1 | 10/2003 | Kakuta et al. |
| 2004/0028681 A1 | 2/2004 | Ito et al. |
| 2004/0037803 A1 | 2/2004 | Sato |
| 2004/0115197 A1 | 6/2004 | Yoshizaki et al. |
| 2004/0191243 A1 | 9/2004 | Chen |
| 2004/0197324 A1 | 10/2004 | Liu et al. |
| 2005/0004354 A1 | 1/2005 | Salfeld et al. |
| 2005/0118163 A1 | 6/2005 | Mizushima et al. |
| 2005/0158303 A1 | 7/2005 | Liu et al. |
| 2005/0175603 A1 | 8/2005 | Liu et al. |
| 2005/0175611 A1 | 8/2005 | Mahler et al. |
| 2005/0214278 A1 | 9/2005 | Kakuta et al. |
| 2005/0238644 A1 | 10/2005 | Mihara et al. |
| 2006/0127975 A1 | 6/2006 | Link et al. |
| 2006/0134113 A1 | 6/2006 | Mihara |
| 2006/0142549 A1 | 6/2006 | Takeda et al. |
| 2006/0165696 A1 | 7/2006 | Okano et al. |
| 2006/0251653 A1 | 11/2006 | Okuda et al. |
| 2006/0292147 A1 | 12/2006 | Yoshizaki et al. |
| 2007/0036785 A1 | 2/2007 | Kishimoto et al. |
| 2007/0053900 A1 | 3/2007 | Liu et al. |
| 2007/0086995 A1 | 4/2007 | Liu et al. |
| 2007/0098714 A1 | 5/2007 | Nishimoto et al. |
| 2007/0116700 A1 | 5/2007 | Liu et al. |
| 2007/0122402 A1 | 5/2007 | Bolli et al. |
| 2007/0134242 A1 | 6/2007 | Nishimoto et al. |
| 2007/0148169 A1 | 6/2007 | Yoshizaki et al. |
| 2007/0184050 A1 | 8/2007 | Ishikawa et al. |
| 2008/0124325 A1 | 5/2008 | Ito et al. |
| 2008/0124761 A1 | 5/2008 | Goto et al. |
| 2008/0274106 A1 | 11/2008 | Nishimoto et al. |
| 2008/0306247 A1 | 12/2008 | Mizushima et al. |
| 2009/0022719 A1 | 1/2009 | Mihara et al. |
| 2009/0061466 A1 | 3/2009 | Hoesel et al. |
| 2009/0131639 A1 | 5/2009 | Kakuta et al. |
| 2009/0181029 A1 | 7/2009 | Okuda et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2009/0280129 A1 | 11/2009 | Liu et al. |
| 2009/0291076 A1 | 11/2009 | Morichika et al. |
| 2009/0304706 A1 | 12/2009 | Lu et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129355 A1 | 5/2010 | Ohguro et al. |
| 2010/0158898 A1 | 6/2010 | Liu et al. |
| 2010/0247523 A1 | 9/2010 | Kano et al. |
| 2010/0255007 A1 | 10/2010 | Mihara et al. |
| 2010/0285011 A1 | 11/2010 | Morichika et al. |
| 2010/0304400 A1 | 12/2010 | Stubenrauch et al. |
| 2011/0098450 A1 | 4/2011 | Igawa et al. |
| 2011/0117087 A1 | 5/2011 | Franze et al. |
| 2011/0150869 A1 | 6/2011 | Mitsunaga et al. |
| 2011/0206664 A1 | 8/2011 | Yoshizaki et al. |
| 2011/0245473 A1 | 10/2011 | Igawa et al. |
| 2011/0262462 A1 | 10/2011 | Platt et al. |
| 2011/0268734 A1 | 11/2011 | Ito et al. |
| 2012/0009177 A1 | 1/2012 | Platt et al. |
| 2012/0064086 A1 | 3/2012 | Liu et al. |
| 2012/0076783 A1 | 3/2012 | Liu et al. |
| 2012/0183539 A1 | 7/2012 | Maeda |
| 2012/0219974 A1 | 8/2012 | Stubenrauch et al. |
| 2012/0253016 A1 | 10/2012 | Igawa et al. |
| 2012/0301460 A1 | 11/2012 | Bao et al. |
| 2013/0149302 A1 | 6/2013 | Mitsunaga et al. |
| 2013/0202588 A1 | 8/2013 | Nishimura |
| 2013/0209456 A1 | 8/2013 | Kano et al. |
| 2013/0225796 A1 | 8/2013 | Takeda et al. |
| 2013/0317203 A1 | 11/2013 | Igawa et al. |
| 2014/0005367 A1 | 1/2014 | Morichika et al. |
| 2014/0017236 A1 | 1/2014 | Okuda et al. |
| 2014/0056883 A1 | 2/2014 | Zhang et al. |
| 2014/0056884 A1 | 2/2014 | Zhang et al. |
| 2014/0056885 A1 | 2/2014 | Zhang et al. |
| 2014/0079695 A1 | 3/2014 | Nishimoto et al. |
| 2014/0323695 A1 | 10/2014 | Takeda et al. |
| 2014/0377254 A1 | 12/2014 | Kano et al. |
| 2015/0010554 A1 | 1/2015 | Okuda et al. |
| 2015/0037319 A1 | 2/2015 | Lau et al. |
| 2018/0344630 A1 | 12/2018 | Igawa et al. |

(56) References Cited

U.S. PATENT DOCUMENTS

| | | |
|---|---|---|
| 2019/0358323 A1 | 11/2019 | Liu et al. |
| 2020/0079857 A1 | 3/2020 | Morichika et al. |

FOREIGN PATENT DOCUMENTS

| | | |
|---|---|---|
| CN | 1849135 A | 10/2006 |
| CN | 101111264 A | 1/2008 |
| CN | 101420972 4 | 4/2009 |
| CN | 101426817 A | 5/2009 |
| EC | SP07-7308 | 3/2007 |
| EC | SP08-8159 | 3/2008 |
| EP | 0 628 639 | 12/1994 |
| EP | 1977763 A1 | 10/2008 |
| EP | 2526963 | 11/2012 |
| EP | 3718531 A1 | 11/2018 |
| JP | 3630453 | 3/1995 |
| JP | 3822137 | 11/2003 |
| JP | 2005527503 A | 9/2005 |
| JP | 2007511566 A | 5/2007 |
| JP | 2007204498 A | 8/2007 |
| JP | 2009092508 | 4/2009 |
| JP | 2011/068675 | 4/2011 |
| WO | 0010607 | 3/2000 |
| WO | 01/24814 | 4/2001 |
| WO | 01/64241 A1 | 9/2001 |
| WO | 0213860 A1 | 2/2002 |
| WO | 2002013859 | 2/2002 |
| WO | 02/17957 A1 | 3/2002 |
| WO | 2003068259 | 8/2003 |
| WO | 2003068260 | 8/2003 |
| WO | 03/072060 A2 | 9/2003 |
| WO | WO 2004/039826 | 5/2004 |
| WO | 2004/091658 A1 | 10/2004 |
| WO | 2004096273 A1 | 11/2004 |
| WO | WO 2005/058365 | 6/2005 |
| WO | WO 2005/077414 | 8/2005 |
| WO | 2006/044908 A2 | 4/2006 |
| WO | WO 2006/081587 | 8/2006 |
| WO | 2007/019232 A2 | 2/2007 |
| WO | 2007/074880 A1 | 7/2007 |
| WO | 2007/109221 | 9/2007 |
| WO | WO 2007/124299 | 11/2007 |
| WO | 2008016134 | 2/2008 |
| WO | 2008/086395 | 7/2008 |
| WO | 2008078715 | 7/2008 |
| WO | 2009084659 | 7/2009 |
| WO | 2011149046 | 12/2011 |
| WO | 2011149051 | 12/2011 |
| WO | 2012064627 | 5/2012 |
| WO | 2013031237 | 3/2013 |
| WO | 2018060210 A1 | 4/2018 |
| WO | 2018078162 A1 | 5/2018 |

OTHER PUBLICATIONS

Examination Decision on Invalidation Request, State Intellectual Property Office of the People's Republic of China, Patent No. 200880119066.5, dated Jan. 6, 2021, with English translation.
"Biotechnology Pharmaceutical Preparations," Textbooks of Continuing Education of National Licensed Pharmacist, published by China Press of Traditional Chinese Medicine, Beijing, China, pp. 338-339, 2007, with partial translation.
"Preparation Techniques for Pharmaceutical Preparations and DDS of Biotechnology-Based Drugs: Conventional injections for proteins and peptides," Pharmaceutics, Pharmaceutical Textbook of Peking University, pp. 610-611,2006 with partial translation.
Declaration of Dr. Masakuzu Fukuda, submitted to the China National Intellectual Property Administration (CNIPA) on Dec. 30, 2019, with translation.
Declaration of Yuka Funakoshi, submitted to the USPTO dated Dec. 6, 2017, in U.S. Appl. No. 14/963,414.
Declaration of Yoshimi Imaeda Under 37 CFR 1.132, submitted to the USPTO dated Dec. 6, 2017, in U.S. Appl. No. 14/963,414.

Mahler et al., "Protein Aggregation: Pathways, Induction Factors and Analysis," J. Pharm. Sci 98:2909-2934 (2009).
Vlasak and Ionescu, "Heterogeneity of Monoclonal Antibodies Revealed by Charge-Sensitive Methods," Cur. Pharm. Biotech. 9:468-481 (2008).
Interlocutory decision in Opposition proceedings, Opposition Division, European Patent Office, in Application No./ Patent No. 08 866 971.8/2 238 985, dated Jan. 2, 2020.
Decision of Technical Board of Appeal 3.3.07, Boards of Appeal, European Patent Office, in European Patent No. 2238985, dated Dec. 11, 2018.
Data of Yuka Funakosh, filed in Japanese Patent Office, Application No. 2015-223070, on Apr. 3, 2017, with translation.
Submission with data, filed in China National Intellectual Property Administration (CNIPA), Application No. 20080119066.5, on May 2, 2013, with partial translation.
Affidavit of Yuka Funakoshi, filed in Indian Patent Office, Application No. 4527/CHENP/2010, on Dec. 12, 2016.
Affidavit of Yoshimi Imaeda, filed in Indian Patent Office, Application No. 4527/CHENP/2010, on Dec. 12, 2016.
Demeule et al., Where disease pathogenesis meets protein formulation: renal deposition of immunoglobulin aggregates, European Journal of Pharmaceutics and Biopharmaceutics, 62:121-130 (2006).
Ha et al., Peroxide formation in polysorbate 80 and protein stability, 91(10):2252-2264 (2002).
Hermeling et al., Structure-Immunogenicity Relationships of Therapeutic Proteins, Pharmaceutical Research, 21 (6):897-903 (2004).
Kroon et al., Identification of sites of degradation a therapeutic monoclonal antibody by peptide mapping, Pharmaceutical Research, 9(11):1386-1393 (1992).
Lam et al., Antioxidants for Prevention of Methionine Oxidation in Recombinant Monoclonal Antibody HER2, Journal of Pharmaceutical Sciences, 86(11):1250-1255 (1997).
Paborji et al., Chemical and physical stability of chimeric L6, a mouse-human monoclonal antibody, Pharmaceutical Research, 11(5):764-771 (1994).
Patten et al., The immunogenicity of biopharmaceuticals. Lessons learned and consequences for protein drug development, Dev. Biol, 112:81-97 (2003) Abstract.
Ryan et al., Averse Effects of Intravenous Immunoglobulin Therapy, Clinical Pediatrics, p. 23 (1996).
Shire et al., Challenges in the development of high protein concentration formulations, Journal of Pharmceutical sciences, 93(6):1390-1391 (2004).
Sukumar et al., Opalescent appearance of an IgG1 antibody at high concentrations and its relationship to noncovalent association, Pharmaceutical Research, 21(7):1087-1093 (2004).
Treuheit et al., Inverse relationship of protein concentration and aggregation, Pharmaceutical Research, 19 (4):511-516 (2002).
Wang et al., Antibody structure, instability, and formulation, Journal of Pharmaceutical Sciences, 96(1):1-26 (2007).
Zheng et al., Influence of pH, buffer species, and storage temperature on physicochemical stability of a humanized monoclonal antibody LA298, International Journal of Pharmaceutics, 308:46-51 (2006).
Braun et al., Protein Aggregates seem to play a key role among the parameters influencing the antigenicity of interferon alpha (IFN-alpha) in normal and transgenic mice, Pharmaceutical Research, 14(10):1472-1478 (1997).
Declaration of Y. Imaeda, submitted in European Patent Office, in European Patent No. 2238985, dated Jan. 27, 2014.
Lenting, et al., "Emicizumab, a bispecific antibody recognizing coagulation factors IX and X: how does it actually compare to factor VIII?" (2017), online at http://www.bloodjournal.org/content/early/2017/10/17/blood-2017-08-801662?sso-checked=true, accessed Dec. 5, 2017, pp. 1-6.(abstract only).
Meulenbroek, et al., "2.3 Properties of human IgG subclasses" (1996), online at https://ednieuw.home.xs4all.nl/IgGsubclasses/subkl23.htm ; accessed Dec. 5, 2017, pp. 1-7.
Gokarn, et al., Excipients for Protein Drugs, Excipient Development for Pharmaceutical, Biotechnology, and Drug Delivery Systems, First Edition Ed. Katdare & Chaubal, 2006, pp. 291-306 and appendix pp. 1-25, chapter 17.

(56) References Cited

OTHER PUBLICATIONS

Nishimoto, et al., Anti-interleukin 6 receptor antibody treatment in rheumatic disease, Ann. Rheum. Dis., 2000, pp. i21-i27, 59(suppl I).
Sato, et al., Reshaping a Human Antibody to Inhibit the Interleukin 6-dependent Tumor Cell Growth, Cancer Research, Feb. 15, 1993, pp. 851-856, vol. 53.
European Medicines Agency, Excerpt from Annex I: Summary of Product Characteristics for "ReFacto AF" except p. 2 (obtained from European Medicines Agency website http://www.ema.europa.eu/ema/), as filed in the proceedings on European Application No. EP 08 86 6971.8 on Jan. 17, 2014.
Chemical Abstract Sergice, CAS Registry No. 375823-41-9 Information excerpt, https://stnweb-japan.cas.org/cgi-bin/sdcgi?SID=541745-1423415591-300&APP=stnw . . . , Immunoglobulin G1, anti (human interleukin 6 receptor) (human-mouse monoclonal MRA heavy chain), disulfide with human-mouse monoclonal MRA k-chain, dimer, Feb. 2, 2012, pp. 1-6.
Declaration of Dr. Masakazu Fukuda, signed May 27, 2015, pp. 1-3, as filed in the proceedings on European Application No. EP 08 86 6971.8 on May 29, 2015.
CV of Tejash Shah, pp. 1-2, as filed in the proceedings on European Application No. EP 08 86 6971.8 on May 29, 2015.
Chugai Seiyaku, et al., English translation of priority document JP 2007-336310, as filed in the proceedings on European Application No. EP 08 86 6971.8 on Jun. 23, 2015.
Glaxo Group Limited, English translation of priority document JP 2007-336310, as filed in the proceedings on European Application No. EP 08 86 6971.8 on Jun. 22, 2015.
Imaeda Declaration, filed in Opposition Proceeding on EP 8866971.8 (executed Jan. 15, 2014).
Liu, et al., U.S. Appl. No. 14/201,346, filed Mar. 7, 2014 (not yet published) (counterpart of USP 6,875,432, previously of record; USP 7,666,413, of record this IDS reference 2; etc.; hence cumulative).
Igawa, et al., U.S. Appl. No. 14/520,423, filed Oct. 22, 2014 (not yet published) (counterpart of USP 8,562,991, of record this IDS reference 11; etc., hence cumulative).
Chugai, et al., "Launch of Subcutaneous Injection formulation Actemra, for a Treatment of Rheumatoid Arthritis the First Anti-IL-6 Receptor Antibody in Subcutaneous market", May 24, 2013, pp. 1-2, submitted as exhibits to Patentee Chugai's Jan. 17, 2014 observations on Opposition by Glaxo Limited to EP 08 86 6971.8/EP-B9 2238985.
Chugai, et al., Annex 1, Summary of Product Characteristics, pp. 1-2, Nov. 15, 2013, submitted as exhibits to Patentee Chugai's Jan. 17, 2014 observations on Opposition by Glaxo Limited to EP 08 86 6971.8/EP-B9 2238985.
Chugai, et al., Declaration of Yoshimi Imaeda, Jan. 15, 2014, pp. 1-2., submitted as exhibits to Patentee Chugai's Jan. 17, 2014 observations on Opposition by Glaxo Limited to EP 08 86 6971.8/EP-B9 2238985.
Patentee Chugai's Jan. 17, 2014 observations on Opposition by Glaxo Limited to Application No. EP 08 86 6971.8/EP-B9 2238985.
Chang, et al., Practical Approaches to Protein Formulation Development, chapter 1 in Carpenter and Manning; Rational Design of Stable Protein Formulations, 2002, pp. 1-25.
Daugherty, et al., Formulation and delivery issues for monoclonal antibody therapeutics, Advanced Drug Delivery Reviews, 2006, pp. 686-706, vol. 58.
Lam, et al., Antioxidants for Prevention of Methionine Oxidation in Recombinant Monoclonal Antibody HER2, Journal of Pharmaceutical Sciences, Nov. 1997, pp. 1250-1255, vol. 86, No. 11.
Nayar, et al., High Throughput Formulation: Strategies for Rapid Development of Stable Protein Products, chapter 8 in Carpenter and Manning; Rational Design of Stable Protein Formulations, 2002, pp. 177-198.
Glaxo Group Limited, Notice of Opposition to European patent EP 2238985, European Patent Office (May 29, 2013).
ACTEMRA (Tocilizumab) , Highlights on Prescribing Information, pp. 1-31 (Oct. 2012).
Masakazu Fukuda and Yoshimi Imaeda, et al., Additional Study for the Chinese Patent Application for MRAsc formulation (Apr. 5, 2013), Chugai Internal Memorandum.
Genentech Press Release, "Genentech Reports Positive Study of ACTEMRA Given by Subcutaneous Injection", (May 2, 2012) [accessed Apr. 18, 2013].
"9493.Tocilizumab: The Merck Index", The Merck Index [Online] http://www.medicinescomplete.com/mc/merck/current/09493.htm?q=actemra&t=search&ss . . . [accessed Apr. 8, 2013].
Nakahara et al. (2003), Arthritis & Rheumatism, vol. 48, pp. 1521-1529.
Huali Wu, "Progress in research on stability of freeze-dried formulations", *Chinese Pharmaceutical Journal*, vol. 36 (7) , pp. 436-438, 2001.
Extended European Search Report dated Dec. 13, 2010 for European Application No. 08866971.8.
English Translation of Korean Official Action dated Apr. 1, 2011, for Korean Patent Application No. 2010-7016322.
Abstract of Ecuadorian Patent No. SP07-7440.
Abstract of Ecuadorian Patent No. SP07-7702.
Opposition to Ecuador Application No. SP-1O-10370 (In Spanish with English Translation).
http://www.ub.edu/legmh/capitols/sunyenegre.pdf [internet] (In Spanish with partial English translation).
http://es.wikipedia.org/wiki/Forma_gal%C3%A9nica [Internet Wikepedia] (In Spanish with partial English translation), downloaded Mar. 9, 2011.
http://intranet.comunidadandina.org/documentos/Gacetas/gace722.pdf [internet] (In Spanish with partial English translation) published Oct. 12, 2001.
http://intranet. comunidadandina.org/Documentos/Procesos/21-ip-2000.doc [internet] (In Spanish with partial English translation) published Oct. 27, 2000.
Chelius et al. "Identification and Characterization of Deamidation Sites in the Conserved Regions of Human Immunoglobulin Gamma Antibodies" Anal. Chem, 77; pp. 6004-6011 (2005).
International Preliminary Report on Patentability (Form PCT/IB/373) issued in PCT/JP2008/073798.
Written Opinion (Form PCT/ISA/237) issued in PCT/JP2008/073798.
Tsumoto K, Umetsu M. Kumagai I. Ejima D, Philo JS, Arakawa T. Role of arginine in protein refolding, solubilization, and purification, Siotcchnol Prog, 20:1301-8 (2004).
Baynes BM, Wang DIC, Trout BL., Role of arginine in the stabilization of proteins against aggregation, Biochemistry, 44: 4919-25 (2005).
Fukuda M, Kameoka D, Torizawa T, Saitoh S, Yasutake M, Imaeda Y, Koga A, Mizutani A, Thermodynamic and fluorescence analyses to determine mechanisms of IgG1 stabilization and destabilization by arginine, Pharm. Res., 31:992-1001 (2014).
Van Reis R, Zydney A., Membrane separations in biotechnology, Curr Opin Biotechnol., 12: 208-211 (2001).
Suki A, Fane AG, Fell CJD, Flux decline in protein ultrafiltration, J. Membr. Sci., 21: 269-283 (1984).
Van Reis R, Zydney A, Bioproccss membrane technology, J Mem Sci, 297:16-50 (2001).
Cromwell ME, Hilario E, Jacobson F., Protein aggregation and bioprocessing, AAPS J., 8: E572-579 (2006).
Bolton GR. Boesch AW, Basha J. Lacasse DP, Kelley BD, Acharya H., Effect of protein and solution properties on the Donnan effect during the ultrafiltration of proteins, Biotechnol Prog.,27:140-152 (2011).
Yoshimi Imaeda et al., "The development of ACTEMRA 162 mg Syringe/Auto Injector for SG Injection", PDA Journal of GMP and Validation in Japan, vol. 19, No. 2 (2017) with English Translation.
Shiloach et al., "Tangential Flow Filtration," Adv Biotechnol Process, 8:97-125 (1988).
Daugherty et al., Formulation and delivery issues for monoclonal antibody therapeutics, Advanced Drug Delivery Reviews, vol. 58 pp. 686-706 (Year: 2006).

HIGH CONCENTRATION ANTIBODY-CONTAINING LIQUID FORMULATION

TECHNICAL FIELD

The present invention relates to an antibody-containing formulation, and particularly, to a stable liquid formulation containing a high concentration of an antibody.

BACKGROUND ART

In recent years, various antibody formulations have been developed and used in practice. Many such antibody formulations are used in intravenous injection. However, due to needs of a clinical site, there is an increasing demand for development of an antibody-containing formulation that can be administered as a self-injectable subcutaneous injection.

In designing an antibody-containing formulation for subcutaneous injection, since a dose of an antibody per administration is large (about 100 mg to 200 mg) and an amount of an injection solution is generally limited in subcutaneous injection, it is necessary to increase a concentration of an antibody in a liquid to be administered. In view of this, in many cases, high concentration formulations are used, which are prepared by the lyophilization-concentration technique, in which a lyophilized formulation is reconstituted in water having a volume smaller than that before lyophilization. However, a strong demand exists for a liquid formulation which does not require reconstitution, and which is easy to handle. Although an increase in a viscosity of a formulation due to addition of a cryoprotective agent such as a sugar in the production process of the lyophilized formulation is not preferred for formulations for subcutaneous injection, it is surmised that this problem could be avoided if the formulation were a liquid formulation.

Solutions containing a high concentration of an antibody tend to form solutions having a high viscosity due to macrcmolecular properties of proteins, and due to the intermolecular interactions of proteins. Further, in cases where a protein is stored in a form of a solution having a high concentration, problematic degradation occurs, which includes a generation of insoluble and/or soluble aggregates; and it is necessary to prevent such degradation. Especially, in antibody formulations, associations are likely to be formed and insoluble aggregates are likely to be generated in a liquid state. In cases where a liquid formulation is stored for a long time, a problem exists in that a bioactivity of antibody molecules is lost due to deamidation of amino acid residues such as asparagine residues.

There have been proposed various ideas for providing a stabilized formulation, in which loss of an active component is small even after the formulation is stored for a long period of time. Such formulations are produced by dissolving an active component and various additives in a buffer solution. However, for liquid formulations containing a high concentration of an antibody, there does not yet exist a technology that is sufficient to prevent dimerization and deamidation.

A need to provide a high concentration antibody-containing formulation exists, in which dimerization and deamidation during long-term storage are inhibited, and which is both stable and suitable for use in subcutaneous administration.

DISCLOSURE OF THE INVENTION

Problem to be Solved by the Invention

An object of the present invention is to provide a high concentration antibody-containing liquid formulation, in which dimerization and deamidation during long-term storage are inhibited, and which is stable and suitable for use in subcutaneous administration.

MEANS FOR SOLVING TILE PROBLEM

The present inventors conducted intensive study with a view to attaining the above object, and as a result, discovered that a stable high concentration antibody-containing liquid formulation can be provided by adding an amino acid, arginine or a salt thereof, as a stabilizer, to thereby complete the present invention.

That is, the present invention provides the following:
(1) A stable antibody-containing liquid formulation, characterized by comprising arginine and methionine.
(2) The formulation of (I) further comprising a histidine buffering agent.
(3) The formulation of (1) or (2) further comprising a surfactant.
(4) The formulation according to (1) to (3) containing the antibody in an amount of at least 50 mg/ml.
(5) The formulation according to (1) to (3) containing the antibody in an amount of at least 100 mg/ml.
(6) The formulation according to (1) to (3) containing the antibody in an amount of at least 120 mg/ml.
(7) The formulation according to (1) to (6) wherein the antibody is an anti-IL-6 receptor antibody.
(8) A stable liquid formulation containing an anti-IL-6 receptor antibody, characterized by comprising either arginine or methionine.
(9) The formulation according to (1) to (8) wherein the antibody is a humanized antibody or human antibody.
(10) The formulation according to (1) to (9) further comprising tryptophane.
(11) The formulation according to (1) to (10) having the pH in the range from 4 to 8.
(12) The formulation according to (1) to (11) wherein the arginine is present in an amount of from 50 to 1500 mM.
(13) The formulation according to (1) to (12) having a viscosity of from 2 to 15 mPa·s.
(14) The formulation according to (1) to (13), which is stable at 22-28° C. for at least 6 months.
(15) The formulation according to (1) to (13), characterized in that dimerization of antibody molecules is inhibited.
(16) The formulation according to (1) to (13), characterized in that deamidation of antibody molecules is inhibited.
(17) The formulation according to (1) to (13), which is for subcutaneous administration.
(18) The formulation according to (1) to (13) which has not been subjected to lyophillization during preparation of the formulation.
(19) A method for inhibiting deamidation of molecules of an antibody in a liquid formulation containing the antibody, comprising adding arginine to the liquid formulation.
(20) A method for inhibiting dimerization of molecules of an antibody in a liquid formulation containing the antibody, comprising adding arginine and methionine to the liquid formulation.

Advantages of the Invention

By the present invention, a liquid formulation containing a high concentration of an antibody is provided, with which reformulation by concentration by lyophilization is not necessary, and hence does not require reconstitution. The antibody-containing liquid formulation according to the present invention can be stored in a liquid state for a long time. Since the antibody-containing liquid formulation according to the present invention can be produced by a process not including a lyophilization step, addition of a sugar or the like as a cryopmtective agent is not necessary.

BEST MODE FOR CARRYING OUT THE INVENTION

Figure 1:
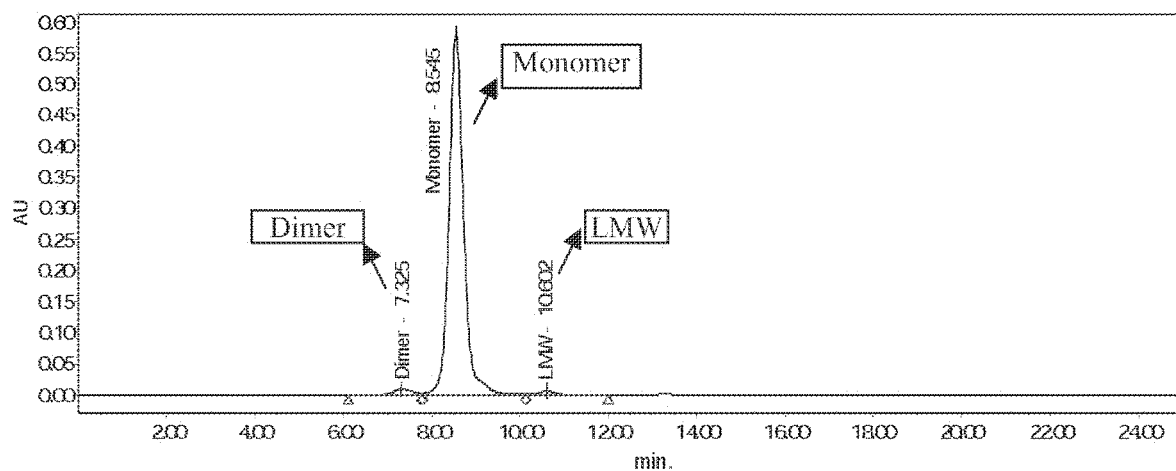
FIG. 1 shows a typical chromatogram of Example 1.

The present invention will now be described in detail.

In the present invention, "antibody-containing liquid formulation" means a liquid formulation containing an antibody as an active component, which is prepared such that it can be administered to an animal such as human, and which is preferably produced by a process not including a lyophilization step.

The antibody-containing liquid formulation according to the present invention is a liquid pharmaceutical formulation containing an antibody at a high concentration, which preferably has an antibody concentration of not less than 50 mg/mL, more preferably not less than 100 mg/mL, still more preferably not less than 120 mg/mL, and yet more preferably not less than 150 mg/mL. It should be noted that a liquid formulation containing antibody at a concentration of 120 mg/mL or higher, or preferably 150 mg/mL or higher, has not been developed for commercial use. Namely, the present invention allows for the first time to put to use a liquid formulation containing antibody at this high concentration.

Further, considering the manufacturing process, the highest concentration of antibody in the liquid formulation according to the present invention may be typically 300 mg/mL., preferably 250 mg/mL, and more preferably 200 mg/mL. Therefore, the antibody-containing liquid formulation according to the present invention preferably has an antibody concentration of from 50 to 300 mg/mL, more preferably from 100 to 300 mg/mL, still more preferably from 120 to 250 mg/mL, and yet more preferably from 150 to 200 mg/mL.

The antibody to be used in the present invention is not restricted as long as it binds to a desired antigen. The antibody can be either a polyclonal antibody or a monoclonal antibody, although a monoclonal antibody is preferred because an antibody having uniform properties can be produced stably.

A monoclonal antibody which can be used in the present invention includes not only monoclonal antibodies originated from an animal such as human, mouse, rat, hamster, rabbit, sheep, camel or monkey, but also includes artificially modified recombinant antibodies such as chimeric antibody, humanized antibody and bispecific antibody. The immunoglobulin class of the antibody is not restricted, and can be any of the classes including IgGs such as IgG1, Ig2, Ig3 and IgG4, igA, IgD, IgE and IgM. Among these classes, IgG and igM are preferred.

The antibody which can be used in the present invention includes not only whole antibodies, but also antibody fragments such as Fv, Fab and F(ab)$_2$; and low molecular weight antibodies such as single chain Fv (scFv, sc(Fv)$_2$, diabodies such as scFv dimer) having one or more specificities, prepared by binding the variable regions of an antibody through a linker such as a peptide linker.

The above-described antibodies which can be used in the present invention can be prepared by methods well known to those skilled in the art.

A hybridoma producing a monoclonal antibody can be prepared as follows basically utilizing a known technique. That is, the hybridoma can be prepared by immunizing an animal with a desired antigen or cells expressing the desired antigen as a sensitizing antigen by a standard method; fusing the obtained immunocytes with known parent cells by a standard cell-fusion method; and screening a monoclonal antibody-producing cell (hybridoma) by a standard screening method. Preparation of a hybridoma can be carried out by, for example, the method according to the method by Milstein et al (Kohler. G. and Milstein, C., Methods Enzymol. (1981) 73: 3-46). In cases where the immunogenicity of the antigen is low, the antigen can be hound to an antigenic macromolecule such as albumin, and the resulting conjugate can be used as an immunogen.

Recombinant antibodies can be employed, which are prepared by the genetic recombination technique in which an antigen gene is cloned from a hybridoma, incorporating the gene into an appropriate vector, introducing the vector into a host, and making the host produce the antibody (see, for example, Carl, A. K. Borrebaeek, James, W. Larrick, THERAPEUTIC MONOCLONAL ANTIBODIES, Published in the United Kingdom by MACMILLAN PUBLISHERS LTD, 1990). More specifically, a cDNA encoding the variable region (V region) in the antibody is synthesized from the mRNA of a hybridoma using a reverse transcriptase. If a DNA encoding the V region of the desired antibody is obtained, the DNA is then ligated to a DNA encoding the constant region (C region) of a desired antibody, and the resulting ligated DNA is introduced into an expression vector. Alternatively, a DNA encoding the V region of the antibody can be incorporated into an expression vector containing the DNA encoding the C region of the antibody. The DNA is incorporated into the expression vector such that the DNA is expressed under the control of an expression-controlling region such as enhancer or promoter. Host cells are then transformed with the resulting expression vector, and the antibody can be expressed by the host cells.

In the present invention, recombinant antibodies artificially modified for the purpose of reducing the heteroantigenicity to human, such as chimeric antibodies and humanized antibodies can be used. These modified antibodies can be produced by known methods. A chimeric antibody is an antibody comprising variable regions in the heavy chain and light chain in an antibody of an animal other than human, such as mouse, and constant regions in the heavy chain and light chain in an antibody of human, and can be obtained by ligating a DNA encoding the variable region in the mouse antibody with a DNA encoding the constant region in the human antibody, incorporating the obtained DNA into an expression vector, introducing the expression vector into a host, and making the host produce the antibody.

Humanized antibody is also called reshaped human antibody, and is obtained by transplanting the CDR (complementarity determining region) of, for example, a mouse antibody to the complementarity determining region of a human antibody. A standard genetic recombination technique for preparing the humanized antibody is also known. Specifically, a DNA designed such that the CDR of the mouse antibody and the framework region (FR) of the human antibody are ligated is synthesized by PCR method from several oligonuclotides prepared so as to have overlapping regions at their terminals. The obtained DNA is ligated to a DNA encoding the constant region of a human antibody, and the resulting DNA is introduced into an expression vector. The expression vector is introduced into a host, and the host is made to produce the humanized antibody (see EP 239400 A and WO 96/02576). As the FR of the human antibody to be ligated through CDR, one of which complementarity determining region forms a good antigen-binding site is selected. As required, an amino acid(s) in the complementarily determining region can be substituted so that the complementarily determining region of the reshaped human antibody forms an appropriate antigen-binding site (Sato, K. et al., Cancer Res. (1993) 53, 851-856).

Methods for obtaining a human antibody are known in the art. For example, a desired human antibody having a binding activity to a desired antigen can be obtained by sensitizing, in vitro, human lymphocytes with the desired antigen or with the cells expressing the desired antigen; fusing the sensitized lymphocytes with human myeloma cells, for example, 11266 cells; and obtaining the antibody from the cells (see JP 1-59878 B). The desired human antibody can also be obtained by immunizing a transgenic animal having all repertories of human antibody genes with the antigen (see WO 93/12227, WO 92/03918, WO 94/02602, WO 94/25585, WO 96/34096 and WO 96/33735). Further, a technique by which a human antibody is obtained by panning using a human antibody library is also known. For example, a variable region of a human body is expressed in the form of a single chain antibody (scFv) on the surface of a phage by use of a phage display method, and the phage which binds to the antigen can be selected. By analyzing the gene of the selected phage, the DNA sequence coding for the variable region of the human antibody which hinds to the antigen can be determined. If the DNA sequence of the scPv which binds to the antigen is determined, an appropriate expression vector containing the sequence is constructed, and the humanized antibody can be obtained. These methods are well known, and WO 92/01047, WO 92/20791, WO 93/06213, WO 93/11236, WO 93/19172, WO 95/01438 and WO 95/15388 can be referred to.

In cases where an antibody gene is once isolated, and the gene is introduced into an appropriate host so as to prepare the antibody, appropriate combinations of the host and expression vector can be used. In cases where eukaryotic cells are used as the host, animal cells, plant cells and fungal cells can be used. Known animal cells include (1) mammalian cells, for example, CHO, COS, myeloma, BHK (baby hamster kidney), Hela and Vero; (2) amphibian cells, for example, *Xenopus* oocytes and (3) insect cells, for example, sf9, sf21 and 'I'n5. Known plant cells include cells originated from plants belonging to the genus *Nicotiana*, for example, *Nicotiana tabacum*, and the cells can be subjected to callus culture. Known fungal cells include the cells originated from yeasts, for example, those belonging to the genus *Saccharomyces* such as Sac charomyces *cerevisiae*; and filamentous bacteria, for example, those belonging to the genus *Aspergillus* such as *Aspergillus niger*. In cases where prokaryotic cells are used, there are production systems using bacterial cells. Known bacterial cells include *E. coli* cells and *Bacillus subtilis* cells. The antibody is obtained by introducing a desired antibody gene into these cells by transformation, and culturing the transformed cells in vitro.

Antibodies in the form of antibody fragments, low molecular weight antibodies and modified antibodies can also be employed as the antibody in the present invention. Examples of the antibody fragments and low molecular weight antibodies include Fab, $F(ab')_2$, Fv, and single chain Fv (scFv, $sc(Fv)_2$ and the like) having one or more specificities, prepared by ligating the Fvs in the H-chain and L-chain through an appropriate linker (Huston, J. S. et al., Proc. Natl. Acad. Sci. U.S.A. (1988) 85, 5879-5883). Specifically, an antibody is treated with papain or pepsin to generate antibody fragments, or a gene encoding these antibody fragments is constructed, and the gene is expressed in appropriate host cells after introducing the gene into an expression vector (see, for example, Co, M. S. et al., T. Immunol. (1994)152, 22968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol, (1986) 121, 652-663; Rousseaux, J. et al., Methods Enzymol. (1986)121, 663-669; Bird, R. E. and Walker, B. W., Trends Biotechnol. (1991) 9, 132-137.

Antibodies bound to various molecules such as polyethylene glycol (PEG) can also be used as modified antibodies. The term "antibody" used in the present invention also includes these modified antibodies. These modified antibodies can be obtained by chemically modifying an obtained antibody. Methods for carrying out the modifications are established in the an.

Examples of the antibody contained in the formulation according to the present invention include, but not limited to, anti-tissue factor antibodies, anti-IL-6 receptor antibodies, anti-IL-6 antibodies, HM1.24 antigen monoclonal antibodies, anti-parathyroid hormone-related peptide antibodies (anti-PTHrP antibodies), anti-glypican-3 antibodies, anti-ganglioside GM3 antibodies, anti-TPO receptor antagonist antibodies, factor VIII-substituting antibodies, anti-CD3 antibodies, anti-CD20 antibodies, anti-GPIIb/IIIa antibodies, anti-TNF antibodies, anti-CD25 antibodies, anti-EGFR antibodies, anti-Her2/neu antibodies, anti-RSV antibodies, anti-CD33 antibodies, anti-CD52 antibodies, anti-IgE antibodies, anti-CD11a antibodies, anti-VEGF antibodies, anti-VLA4 antibodies, anti-AXL antibodies, and so on.

Preferred examples of the reshaped human antibodies used in the present invention include humanized anti-interleukin (II: 6) receptor antibodies (hPM-1 or MRA) (see WO 92-19759), humanized anti-HM1.24 antigen monoclonal antibodies (see WO 98-14580), humanized anti-parathyroid hormone-related peptide antibodies (anti-PTHrP antibodies) (see WO 98-13388), humanized anti-tissue factor antibodies (see WO 99-51743) and anti-glypican-3 humanized IgG Ix antibodies (see PCT/JP05/013103). The humanized antibodies especially preferred in the present invention are humanized anti-IL-6 receptor antibodies.

As the human IgM antibodies, anti-ganglioside GM3 recombinant human IgM antibodies (see WO 05-05636) and the like are preferred.

As the low molecular weight antibodies, anti-TP(:) receptor antagonist diabodies (see WO 02-33072), anti-CI.)47 agonist diabodies (see WO 01-66737) and the like are preferred.

To evaluate the shelf stability of the high concentration antibody-containing liquid formulation, the present inventors studied the effects of various additives by conducting heat acceleration tests and light acceleration tests. As a result, it was found that in solutions in which a high concentration of antibody was dissolved in a buffer solution containing the amino acid arginine, the amount of generated dimer was smaller than that in solutions to which arginine was not added. From these results, it was found that arginine is effective as a stabilizer for inhibiting dimerization. Further, in solutions in which a high concentration of antibody was dissolved in a buffer solution containing arginine and methionine, the inhibitory effect against dimerization was observed at a total concentration of arginine and methionine which is lower than the concentration of arginine alone needed for attaining the same inhibitory effect. From these results, it was found that a synergistic effect is obtained by the addition of arginine and methionine in combination. Further, it was found that deamidation of the antibody molecules is inhibited by the addition of arginine. These results are exemplified as test results obtained for a sample containing a humanized anti-IL-6 receptor antibody at a concentration of 180 mg/ml.

Thus, by adding arginine as a stabilizer, a stable antibody formulation can be provided, in which dimerization of the antibody is reduced and deamidation of the antibody is prevented. Therefore, a first aspect of the present invention is characterized by adding arginine to a solution, whereby dimerization or deamidation of the antibody molecules is inhibited in the resulting antibody-containing liquid formulation. Accordingly, an embodiment as a stable antibody-containing liquid formulation is characterized in that it contains an antibody and arginine in a buffer solution. Further, as described above, an antibody-containing liquid forumulation of the present invention can additionally contain methionine in the solution, with a synergistic effect being obtained by use of arginine and methionine in combination. Therefore, a second aspect of the present invention is characterized by adding arginine and methionine to a solution, whereby dimerization, in particular, of the antibody molecules is inhibited in the resulting antibody-containing liquid formulation. Accordingly, an embodiment as a stable antibody-containing liquid formulation is characterized in that it contains an antibody, arginine and methionine in a buffer solution.

As the arginine used in the present invention, any of the arginine compound per se, derivatives thereof and salts thereof can be used. L-arginine and salts thereof are preferred. As the methionine used in the present invention, any of the methionine compound per se, derivatives thereof and salts thereof can be used. L-methionine and salts thereof are preferred.

In cases where the antibody-containing liquid formulation according to the present invention contains arginine and does not contain methionine, the concentration of arginine is preferably 50 to 15(K) mM, more preferably 1(X) to 1000 mM, still more preferably 2(K) to 700 mM. In cases where the antibody-containing liquid formulation according to the present invention contains arginine and methionine, the total concentration of arginine and methionine is preferably 50 to 1200 mM, for example, preferably, the arginine concentration is 40 to 1000 mM and the methionine concentration is 10 to 200 mM; more preferably, the arginine concentration is 50 to 700 mM and the methionine concentration is 10 to 100 mM; and still more preferably, the arginine concentration is 100 to 300 mM, and the methionine concentration is 10 to 50 mM.

The buffer solution is prepared using a buffering agent which is a substance for maintaining a pH of the solution. In a high concentration antibody-containing liquid formulation according to the present invention, a pH of the formulation is preferably 4 to 8, more preferably 5.0 to 7.5, still more preferably 5.5 to 7.2, and still more preferably 6.0 to 6.5. A buffering agent which can be used in the present invention is one which can adjust the pH in this range and which is pharmaceutically acceptable. Such a buffering agent is known by those skilled in the art, and examples thereof include inorganic salts such as phosphoric acid salts (sodium or potassium) and sodium hydrogen carbonate; organic acid salts such as citric acid salts (sodium or potassium), sodium acetate and sodium succinate; and acids such as phosphoric acid, carbonic acid, citric acid, succinic acid, malic acid and glucosic acid. Further, Tris buffers, Good's buffers such as ME S, MOPS and HEPES, histidine (e.g., histidine hydrochloric acid salt) and glycine can also be used. in the high concentration antibody-containing liquid formulation according to the present invention, the buffer is preferably a histidine buffer or glycine buffer, and a histidine buffer is especially preferred. The concentration of the buffer solution is generally 1 to 500 mM, preferably 5 to 100 mM, still more preferably 10 to 20 mM. In cases where a histidine buffer is used, the buffer solution contains histidine at a concentration of preferably 5 to 25 mM, more preferably 10 to 20 mM.

For the "stable" high concentration antibody-containing liquid formulation according to the present invention, significant change is not observed when it is stored at a refrigeration temperature (2 to 8° C.) for at least 12 months, preferably for 2 years, and more preferably for 3 years; or when it is stored at room temperature (22 to 28° C.) for at least 3 months, preferably 6 months, and more preferably 1 year. For example, sum amount of dimers and degradation products in the formulation when it is stored at 5° C. for 2 years is 5.0% or lower, preferably 2% or lower, and more preferably 1.5% or lower; or sum amount of dimers and degradation products in the formulation when it is stored at 25° C. for 6 months is 5.0% or lower, preferably 2% or lower, and more preferably 1.5% or lower.

The formulation according to the present invention can further contain a surfactant.

Typical examples of the surfactant include nonionic surfactants, for example, sorbitan fatty acid esters such as sorbitan monocaprylate, sorbitan monolaurate and sorbitan monopalmitate; glycerin fatty acid esters such as glycerol monocaprylate, glycerol monomyristate and glycerol monostearate; polyglycerol fatty acid esters such as decaglyceryl monostearate, decaglyceryl distearate and decaglyceryl monolinoleate; polyoxyethylene sorbitan fatty acid esters such as polyoxyethylene sorbitan monolaurate, polyoxyethylene sorbitan monooleate, polyoxyethylenesorbitan monostearate, polyoxyethylene sorbitan monopalmitate, polyoxyethylene sorbitan trioleate and polyoxyethylene sorbitan tristearate; polyoxyethylene sorbitol fatty acid esters such as polyoxyethylene sorbitol tetrastearate and polyoxyethylene sorbitol tetra oleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether, polyoxyethylene polyoxypropylene alkyl ethers such as polyoxyethylene polyoxypropylene glycol ether, polyoxyethylene polyoxypropylene propyl ether and polyoxyethylene polyoxypropylene cetyl ethei;bnlyoxyethylene alkyl phenyl ethers such as polyoxyethylene nonylphenyl ether, polyoxyethylene hardened castor oils such as polyoxyethylene castor oil and polyoxyethylene hardened castor oil (polyoxyethylene hydrogenated castor oil); polyoxyethylene bees wax derivatives such as polyoxyethylene sorbitol bees wax; polyoxyethylene lanolin derivatives such as polyoxyethylene lanolin; surfactants having an 1IL13 of 6 to 18 such as polyoxyethylene fatty acid amides, for example, polyoxyethylene octadecanamide; anionic surfactants, for example, alkyl sulfate salts having a $C_{10}$-$C_{18}$ alkyl group, such as sodium cetyl sulfate, sodium lauryl sulfate and sodium oleyl sulfate; polyoxyethylene alkyl ether sulfate salts in which the average number of moles of the added ethylene oxide units is 2 to 4 and the number of carbon atoms of the alkyl group is it) to 18, such as polyoxyethylene sodium lauryl sulfate; alkyl sulfosuccinate salts having a $C_8$-$C_{18}$ alkyl group, such as sodium lauryl sulfosuccinate; natural surfactants such as lecithin and glycerophospholipids; sphingophospholipids such as sphingomyelin; and sucrose esters of $C_{12}$-$C_{18}$ fatty acids. These surfactants can be added to the formulation of the present, invention individually, or two or more of these surfactants can be added in combination.

Preferred surfactants are polyoxyethylene sorbitan fatty acid esters and polyoxyethylene polyoxypropylene alkyl ethers, and especially preferred are polysorbates 20, 21, 40, 60, 65, 80, 81 and 85, and Pluronic It (high molecular weight polyoxyalkylene ether) type surfactants, and most preferred are polysorbates 20 and 80, and Pluronic F-68 (Poloxamer 188).

The amount of the surfactant(s) to be added to the antibody formulation according to the present invention is generally 0.0001 to 10% (w/v), preferably 0.001 to 5%, more preferably 0.005 to 3%.

In another aspect of the present invention, the formulation according to the present invention is preferably substantially composed of the following components:
  A) anti-IL-6 receptor antibody;
  B) arginine and/or methionine, and additional other amino acid(s) (e.g., tryptophan) as an optional additional component(s);
  C) buffering agent(s); and
  D) surfactant(s).

The term "substantially composed of" herein means that a component other than the components usually added to formulations is not contained, the components usually added to formulations being the optional additive components described below, such as suspending agents, solubilizing agents, isotonic agents, preservatives, adsorption inhibitors, diluents, vehicles, pH-adjusters, soothing agents, sulfur-containing reducing agents and antioxidants.

The above-described "B) arginine and/or methionine, and additional other amino acid(s) (e.g., tryptophan) as an optional additional component(s)" is meant to include the cases where the formulation contains (b-1) arginine; (b-2) arginine and methionine; and (b-3) methionine; respectively, as an amino acid additive(s), and further include the cases where the formulation additionally contains other amino acid(s). Preferred example of the other amino acid(s) is tryptophan. As the tryptophan, any of the tryptophan compound per se, derivatives thereof and salts thereof can be used. L-tryptophan and salts thereof are preferred.

As required, a suspending agent, solubilizing agent, isotonic agent, preservative, adsorption inhibitor, diluent, vehicle, pH-adjuster, soothing agent, sulfur-containing reducing agent, antioxidant and the like can be added to the formulation according to the present invention.

Examples of the suspending agent include methyl cellulose, polysorbate 80, hydroxyethyl cellulose, gum arabic, powdered tragacanth, sodium carboxymethylcellulose and polyoxyethylene sorbitan monolaurate.

Examples of the solubilizing agent include, polyoxyethylene hydrogenated castor oil, polysorbate 80, nicotinamide, polyoxyethylene sorbitan monolaurate, macrogol and castor oil fatty acid ethyl ester.

Examples of the isotonic agent include sodium chloride, potassium chloride and calcium chloride.

Examples of the preservative include methyl p-hydroxybenzoate, ethyl p-hydroxybenzoate, sorbic acid, phenol, cresol and chlorocresol.

Examples of the adsorption inhibitor include human serum albumin, lecithin, dextran, ethyleneoxide-propylene oxide copolymer, hydroxypropylcellulose, methyl cellulose, polyoxyethylene hydrogenated castor oil and polyethylene glycol.

Examples of the sulfur-containing reducing agent include the compounds having a sulfhydryl group(s), such as N-acetylcysteine, N-acetyl hotmocysteine, thioctic acid, thiodiglycol, thioethanolamine, thioglycerol, thiosorbitol, thioglycolic acid and salts thereof, sodium thiosulfate, glutathione and $C_1$-$C_7$ thioalkanes.

Examples of the antioxidant include erythorbic acid, dibutylhydroxytoluene, butylated hydroxyanisole, α-tocopherol, tochpeml acetate, L-ascorbic acid and salts thereof, L-ascorbyl palmitate, L-ascorbyl stearate, sodium hydrogen sulfite, sodium sulfite, triamyl gallate, propyl gallate, and chelating agents such as disodium ethylenediaminetetraacetate (EDTA), sodium pyrophosphate and sodium metaphosphate.

The antibody-containing liquid formulation according to the present invention is usually administered through a parenteral route, for example, by injection (subcutaneous, intravenous, intramuscular injections or the like), percutaneous, transmucosal, transnasal or pulmonary administration, but it can also be administered orally. In subcutaneous injection, the dose of antibody per administration is large (about 100 to 200 mg) while the amount of the injection solution is limited, so that the formulation according to the present invention is especially suited for subcutaneous injection.

The osmotic pressure ratio of the antibody-containing liquid formulation according to the present invention is preferably about 0.5 to 4, more preferably about 0.7 to 2, and still more preferably about 1.

The viscosity of the antibody-containing liquid formulation according to the present invention is preferably about 2 to 15 mPa·s, more preferably about 4 to 10 mPa·s. It should be noted that the viscosity described herein is measured by a rotation viscometer method using a cone-plate type viscometer, in accordance with 2.53 Viscosity Determination/ General Tests, the Japanese Pharmacopoeia, 15th edition.

As can be seen from the results of the examples described below, according to the present invention, a stable liquid formulation can be obtained, in which dimerization and deamidation of the antibody during long-term storage are small, by adding to the formulation arginine alone, or arginine and methionine, or methionine alone.

As another aspect of the present invention, a method for inhibiting deamidation in antibody-containing liquid formulations is provided, the method comprising adding to the formulation arginine or a salt thereof.

As still another aspect of the present invention, a method for inhibiting dimerization of antibody in antibody-containing liquid formulations is provided, the method comprising adding to the formulation arginine and methionine.

In the above-described two methods, the antibody is preferably an anti-IL-6 receptor antibody, which is a humanized antibody or human antibody.

The present invention will now be described in more detail by way of the examples given below. However, the scope of the present invention is not restricted thereto.

EXAMPLES

Antibody Sample

The humanized anti-IL-6 receptor antibody was the humanized antibody prepared in accordance with the method described in Reference Example 2 in JP 8-99902 A using the human elongation factor Ia promoter described in Example 10 in WO 92/19759. This antibody will occasionally be referred to as "MRA" in the tables in Examples.

Example 1

Stabilizing Effects by Combination of Arginine and Methionine Liquid formulations containing anti-IL-6 receptor humanized antibody were evaluated for an influence on stabilization of the formulations obtained by use of a combination of arginine and methionine.

In this study, to evaluate the effects by the combination of arginine and methionine, evaluation samples numbered A1 to A9 were prepared. Prescriptions for the evaluation samples were as follows:

TABLE 1-1

[Prescriptions]

| Sample No. | Antibody mg/mL | Arg mM | Met mM | Polysorbate 80 mg/ml | Histidine buffer mM | pH |
|---|---|---|---|---|---|---|
| A1 | 180 | — | — | 0.5 | 20 | 6.0 |
| A2 | 180 | 50 | — | 0.5 | 20 | 6.0 |
| A3 | 180 | 100 | — | 0.5 | 20 | 6.0 |
| A4 | 180 | 150 | — | 0.5 | 20 | 6.0 |
| A5 | 180 | 200 | — | 0.5 | 20 | 6.0 |
| A6 | 180 | 300 | — | 0.5 | 20 | 6.0 |
| A7 | 180 | 100 | 10 | 0.5 | 20 | 6.0 |
| A8 | 180 | 100 | 30 | 0.5 | 20 | 6.0 |
| A9 | 180 | 100 | 50 | 0.5 | 20 | 6.0 |

To evaluate stability of the liquid formulations, each sample was subjected to a heat acceleration test (stored at 40° C. for 3 months and at 25° C. for 6 months, respectively). The purity of the antibody before and after the heat acceleration test was evaluated by gel permeation chromatography (SEC). The analytical conditions were as follows:

[Gel Permeation Chromatography]

The sample was used as the solution to be measured as it was.

One microliter of the solution to be measured was subjected to liquid chromatography, and the peak areas of the peaks of dimer, monomer and low molecular weight degradation products (LMW) were measured by an automatic analytical method, and the amounts thereof (%) were determined.

[Table 1-2]
Analytical Conditions
Column: TSKgel (33000SWx 1 7.8 mm I. D.×30 cm (TOSOH)
Mobile Phase: phosphate buffer, pH 7.0 (50 mmol/L phosphate buffer, pH 7.0, containing 300 mmol/I, of sodium chloride and 0.05% sodium azide)
Amount of Injected Sample: about 180 µg in terms of humanized anti-IL-6 receptor antibody
Flow Kate: 1 mlJmin
Detection Wavelength: 280 mu
[Formula 1]
Calculation Equation $$\text{Total Area of All Peaks} = \text{Peak Area of Monomer} + \text{Peak Area of Dimer} + \text{Peak Area of Low Molecular Weight Degradation Products (LMW)}$$
$$\text{Amount of Dimer (\%)} = (\text{Peak Area of Dimer}/\text{Total Area of All Peaks}) \times 100$$
$$\text{Amount of Low Molecular Weight Degradation Products (LMW) (\%)} = (\text{Peak Area of Low Molecular Weight Degradation Products}/\text{Total Area of All Peaks}) \times 100$$

A typical chromatography is shown in FIG. 1.

Figure 2:
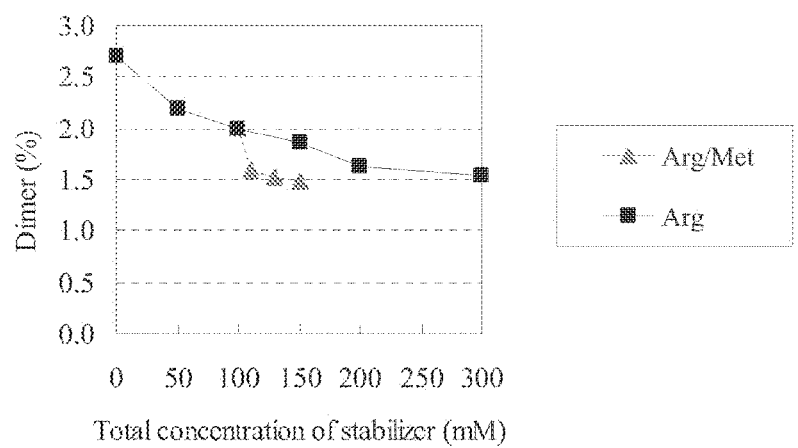
FIG. 2 shows evaluation results of the gel permeation chromatography (SEC) in Example 1.
Figure 3:
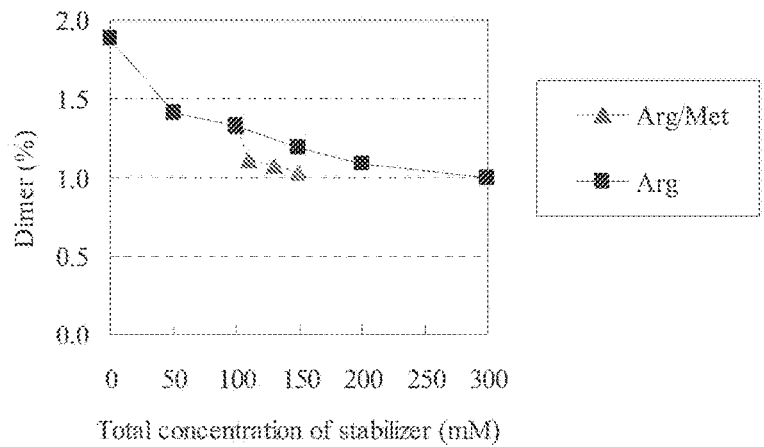
FIG. 3 shows evaluation results of the gel permeation chromatography (SEC) in Example 1.

The evaluation results obtained by the gel permeation chromatography (SEC) are shown in Table 1 and FIGS. 2 and 3. As shown, the amount of dimer in the samples (Sample Nos. A2 to A6) to which arginine was added, after the acceleration at 40° C. for 3 months and at 25° C. for 6 months, respectively, was smaller than that in the sample (Sample No. A 1) to which arginine was not added; and accordingly, the inhibitory effect of arginine against dimerization was confirmed. It was also confirmed that the amount of dimer was reduced proportionally to the amount of the arginine added. On the other hand, the amount of dimer in the samples (Sample Nos. A7 to A9) to which arginine (100 mM) and methionine were added, after the acceleration at 40° C. to 3 months and at 25° C. for 6 months, respectively, was smaller than that in the samples (Sample Nos. A3 and A4) containing 150 mM of arginine, which concentration was about the same as the total concentration of the stabilizers; and the amount of dimer was about the same as in the sample (Sample No. A6) having an arginine concentration of 300 mM. These results are considered to indicate that a synergistic effect in the inhibition of dimerization is obtained by combining arginine and methionine.

Influence of arginine and methionine on the amount of low molecular weight degradation products was not observed.

TABLE 1-3

Table 1

| | 40° C.-3 months | | 25° C.-6 months | |
|---|---|---|---|---|
| | Dimer (%) | LMW (%) | Dimer (%) | LMW (%) |
| A1 | 2.70 | 1.25 | 1.88 | 0.48 |
| A2 | 2.19 | 1.24 | 1.41 | 0.47 |
| A3 | 2.00 | 1.34 | 1.33 | 0.49 |
| A4 | 1.85 | 1.38 | 1.19 | 0.49 |
| A5 | 1.62 | 1.37 | 1.09 | 0.49 |
| A6 | 1.53 | 1.46 | 0.99 | 0.50 |
| A7 | 1.58 | 1.29 | 1.11 | 0.45 |
| A8 | 1.52 | 1.21 | 1.07 | 0.47 |
| A9 | 1.48 | 1.32 | 1.03 | 0.47 |

EXAMPLE 2

Inhibitory Effect by Arginine against Deamidation

Liquid formulations containing anti-IL-6 receptor humanized antibody were evaluated for influence on the deamidation by arginine.

In this study, evaluation samples numbered A 10 to A15 and numbered A16 to A18, containing different amounts of arginine and methionine, respectively, were prepared. Prescriptions for the evaluation samples were as follows:

TABLE 2-1

[Prescriptions]

| Sample No. | Antibody mg/mL | Arg mM | Met mM | Polysorbate 80 mg/ml | Histidine buffer mM | pH |
|---|---|---|---|---|---|---|
| A10 | 180 | — | — | 0.5 | 20 | 6.0 |
| A11 | 180 | 50 | — | 0.5 | 20 | 6.0 |
| A12 | 180 | 100 | — | 0.5 | 20 | 6.0 |
| A13 | 180 | 150 | — | 0.5 | 20 | 6.0 |
| A14 | 180 | 200 | — | 0.5 | 20 | 6.0 |
| A15 | 180 | 300 | — | 0.5 | 20 | 6.0 |
| A16 | 180 | — | 10 | 0.5 | 20 | 6.0 |
| A17 | 180 | — | 30 | 0.5 | 20 | 6.0 |
| A18 | 180 | — | 50 | 0.5 | 20 | 6.0 |

To evaluate the stability of the liquid formulations, each sample was subjected to a heat acceleration test (stored at 40° C. for 3 months and at 25° C. for 6 months, respectively). The purities of the antibody before and after the heat acceleration test were evaluated by ion-exchange chromatography (LEC). The analytical conditions were as follows:

[Ion-exchange Chromatography]

To each sample, purified water was added to adjust the amount of the humanized anti-IL-6 receptor antibody to about 1 mg in 1 mL of the sample, and the resulting sample was used as the sample to be measured.

Thirty microliters of the sample solution was subjected to liquid chromatography, and the peak areas of the peaks of MRA Pre, MRA Main, MRA Sub-1, MRA Sub-22, MRA R-1, 1Q(H)-MRA, 2Q(H)-MRA and other related substances (Others) were measured by an automatic analytical method, and the amounts thereof (%) were determined by an area percentage method.

MRA Pre indicates the total of the peaks of the substances each eluted after a retention time shorter than that of the main component, and a plurality of degradation products, mainly deamidation products of humanized anti-IL-6 receptor antibody, was included. When the production amount of this Pre peak was small, inhibition of deamidation of the antibody is indicated.

[Table 2-2]
Analytical Conditions

Column: ProPac™ WCX-10 4×250 mm chromatography column (DIONEX1, separation materials)

Mobile Phase: Solution A: 25 mntol/I, MES buffer solution, pH 6.1

Mobile Phase: Solution B: 25 mmol/L MES buffer solution, pH 6.1 (containing 250 mtnol/I, of sodium chloride)

Amount of Injected Sample: about 301.1g in terms of humanized anti-IL-6 receptor antibody Flow Rate: 0.5 mL/min Detection Wavelength: 280 nm

[Formula 2]

Calculation Equation

Total Area of All Peaks=Grand Total of Total Area of MRA Pre Peaks+Peak Area of. MRAMain+ Peak Area of MAR Sub-1+Peak Area of MAR Sub-2+Peak Area of MAR Sub-3+Peak Area of MAR R-1+Total Area of 1 Q(H)-MRA Peaks+ Total Area of 2Q(H)-MRA Peaks+Peak Area of Others Amount of MRA Pre (%)=(Total Area of MRA Pre Peaks/Total Area of All Peaks)×100

Figure 4:
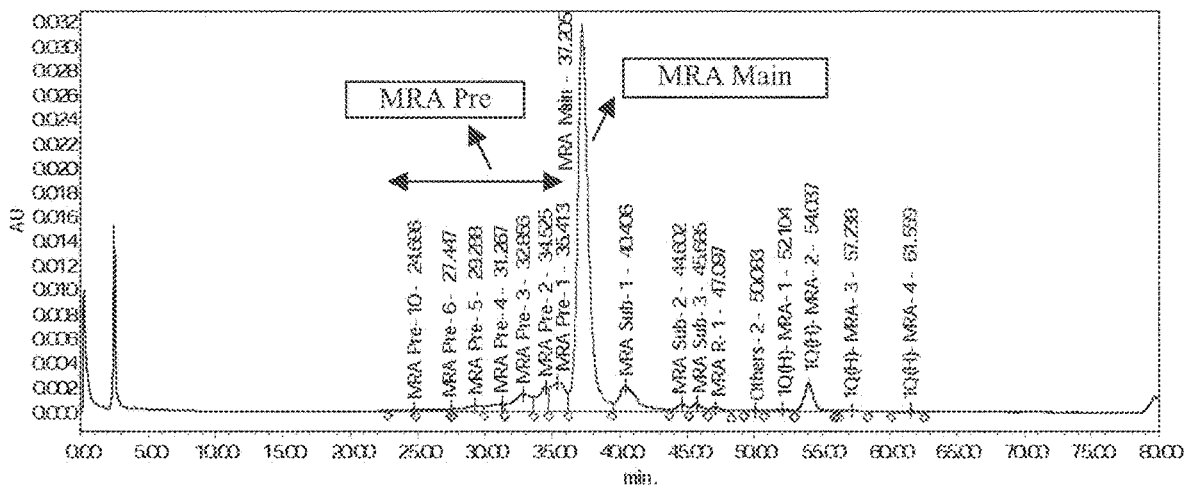
FIG. 4 shows a typical chromatogram of Example 2.

A typical chromatography is shown in FIG. 4. MRA Pre indicates the total of the peaks of the substances appearing earlier than that of the main component.

Figure 5:
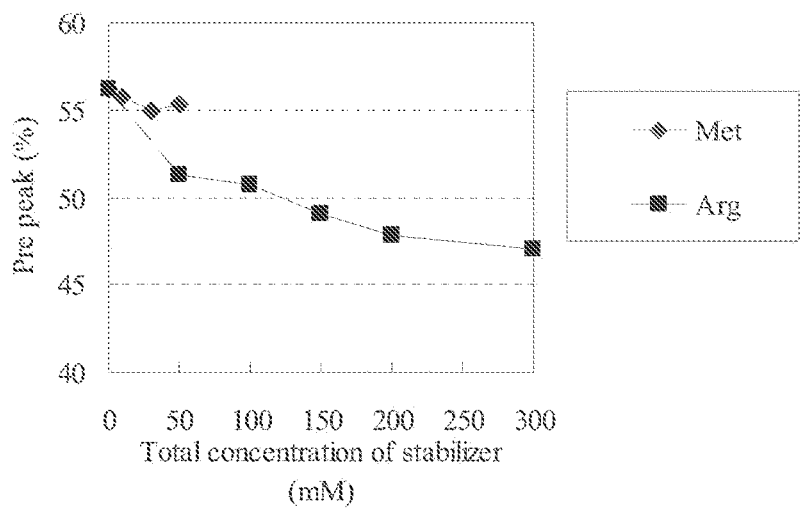
FIG. 5 shows evaluation results of the ion exchange chromatography (lEC) in Example 2.
Figure 6:
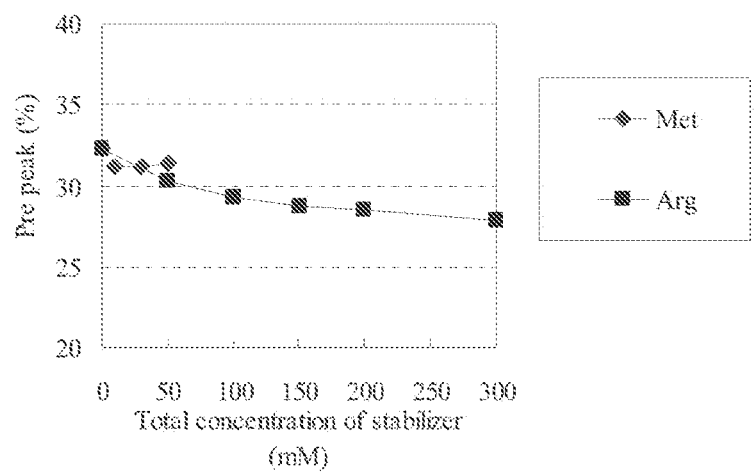
FIG. 6 shows evaluation results of the ion exchange chromatography (IEC) in Example 2.

Evaluation results of the ion-exchange chromatography are shown in Table 2 and FIGS. 5 and 6. As shown, the amount of Pre peaks in the samples (Sample Nos. All to A15) to which arginine was added, after the acceleration at 40° C. for 3 months and at 25° C. for 6 months, respectively, was smaller than that in the sample (Sample No. A10) to which arginine was not added; and accordingly, the inhibitory effect of arginine against the generation of Pre peaks was confirmed. It was also confirmed that the amount of Pre peaks was reduced proportionally to an amount of arginine added. On the other hand, the amount of Pre peaks in the samples (Sample Nos. A 16 to A18) to which methionine was added, after the acceleration at 40° C. for 3 months and at 25° C. for 6 months, respectively, was similar to the sample (Sample No. A10) to which arginine was not added; and accordingly, influence of the addition of methionine was not observed.

TABLE 2-3

Table 2

| | Pre peak (%) | |
|---|---|---|
| | 40° C.-3 months | 25° C.-6 months |
| A10 | 56.2 | 32.3 |
| A11 | 51.3 | 30.3 |
| A12 | 50.7 | 29.3 |
| A13 | 49.0 | 28.7 |
| A14 | 47.8 | 28.5 |
| A15 | 47.0 | 27.9 |
| A16 | 55.7 | 31.2 |
| A17 | 55.0 | 31.2 |
| A18 | 55.3 | 31.4 |

EXAMPLE 3

Stabilizing Effects by Combination of Arginine and Methionine (2)

As in Example 1, liquid formulations containing anti-IL-6 receptor humanized antibody were evaluated for influence on stabilization of the formulations obtained by use of a combination of arginine and methionine.

In this study, to evaluate effects of the combination of arginine and methionine, evaluation samples numbered A 19 to A27 were prepared. Prescriptions for the evaluation samples were as follows:

TABLE 3-1

[Prescriptions]

| Sample No. | Antibody mg/ml | Arg mM | Met mM | Polysorbate 80 mg/ml | Histidine buffer mM | pH |
|---|---|---|---|---|---|---|
| A19 | 180 | — | — | 0.5 | 20 | 6.0 |
| A20 | 180 | 50 | — | 0.5 | 20 | 6.0 |
| A21 | 180 | 100 | — | 0.5 | 20 | 6.0 |
| A22 | 180 | 150 | — | 0.5 | 20 | 6.0 |
| A23 | 180 | 200 | — | 0.5 | 20 | 6.0 |
| A24 | 180 | 300 | — | 0.5 | 20 | 6.0 |
| A25 | 180 | 100 | 10 | 0.5 | 20 | 6.0 |
| A26 | 180 | 100 | 30 | 0.5 | 20 | 6.0 |
| A27 | 180 | 100 | 50 | 0.5 | 20 | 6.0 |

To evaluate the stability of the liquid formulations, each sample was subjected to a light acceleration test (total illuminance 1,200,000lux and total near-ultraviolet radiation energy: 200 W·h/m$^2$). The purities of the antibody before and after the light acceleration test were evaluated by gel permeation chromatography (SEC) and ion exchange chromatography (TEC) as in Examples 1 and 2.

Figure 7:
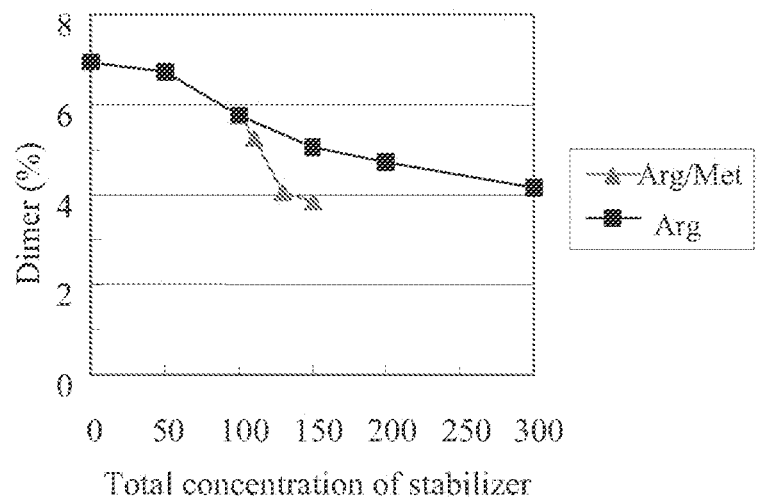
FIG. 7 shows evaluation results of the gel permeation chromatography (SEC) in Example 3.

The evaluation results by the gel permeation chromatography (SEC) are shown in Table 3 and FIG. 7. As shown, the amount of dimer in the samples (Sample Nos. A20 to A24) to which arginine was added, after the light acceleration test was smaller than that in the sample (Sample No. A19) to which arginine was not added; and accordingly, the inhibitory effect of arginine against dimerization was confirmed. It was also confirmed that the amount of dimer was reduced proportionally to an amount of arginine added. On the other hand, the amount of dimer in the samples (Sample Nos. A25 to A27) to which arginine (1(K) mM) and methionine were added, after the light acceleration test was smaller than that in the sample (Sample No. A22) containing 150 mM of arginine, which concentration was about the same as the total concentration of the stabilizers; and the amount of dimer was smaller than in the samples (Sample Nos. A23 and A24) having arginine concentrations of 2(K) mM and 300 mM, respectively. These results are thought to indicate that a synergistic effect in the inhibition of dimerization is obtained by combining arginine and methionine.

Influence of arginine and methionine on the amount of low molecular weight degradation products was not observed.

TABLE 3-2

Table 3

| | 1,200,000 lux + 200 W · h/m$^2$ | |
|---|---|---|
| | Dimer (%) | LMW (%) |
| A19 | 6.95 | 0.22 |
| A20 | 6.75 | 0.24 |
| A21 | 5.78 | 0.21 |
| A22 | 5.08 | 0.19 |
| A23 | 4.73 | 0.18 |

TABLE 3-2-continued

Table 3

| | 1,200,000 lux + 200 W · h/m$^2$ | |
|---|---|---|
| | Dimer (%) | LMW (%) |
| A24 | 4.13 | 0.18 |
| A25 | 5.27 | 0.19 |
| A26 | 4.05 | 0.17 |
| A27 | 3.84 | 0.16 |

Figure 8:
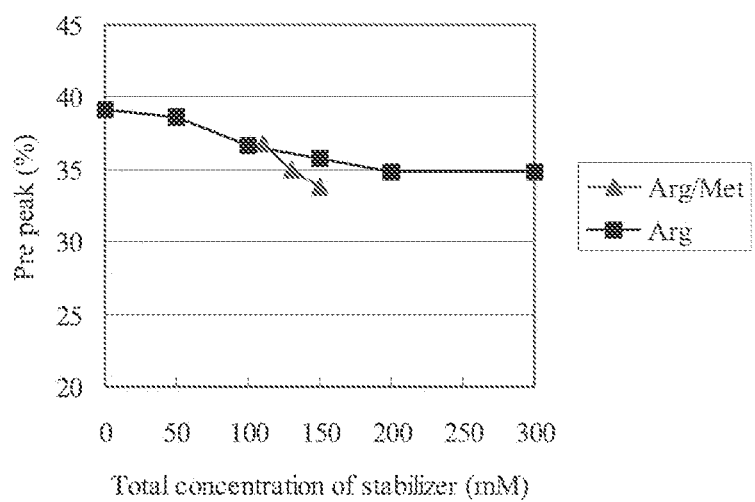
FIG. 8 shows evaluation results of the ion exchange chromatography (TEC) in Example 3.

Next, the evaluation results by the ion exchange chromatography (TIC) are shown in Table 4 and FIG. 8.

As shown, the amount of Pre peak in the samples (Sample Nos. A20 to A24) to which arginine was added, after the light acceleration test was smaller than that in the sample (Sample No. A 19) to which arginine was not added; and accordingly, the inhibitory effect of arginine against formation of Pre peak was confirmed. Further, it was confirmed that as the amount of arginine increases, the production amount of Pre peak decreases proportionately. On the other hand, the amount of dimer after the light acceleration test in the samples (Sample Nos. A25 to A27) to which methionine was further added to arginine (1(X) mM) was smaller than that in the sample (Sample No. A22) containing 150 mM of arginine, which concentration was about the same as the total concentration of the stabilizers; and it was smaller than in the samples (Sample Nos. A23 and A24) having arginine concentrations of 200 nmM and 3(10 mM, respectively. These results are thought to indicate that a synergistic effect in the inhibition of formation of Pre peak by the combination of arginine and methionine.

TABLE 4

| | Pre peak (%) 1,200,000 lux + 200 W · h/m$^2$ |
|---|---|
| A19 | 39.2 |
| A20 | 38.6 |
| A21 | 36.7 |
| A22 | 35.7 |
| A23 | 34.9 |
| A24 | 34.9 |
| A25 | 36.8 |
| A26 | 35.0 |
| A27 | 33.8 |

The invention claimed is:

1. A concentrated liquid formulation comprising 180 mg/mL of a humanized anti-IL-6 receptor antibody MRA, 0.005 to 3% surfactant, and histidine buffer, pH 6.0, wherein the formulation has no more than 2.70% dimers after storage at 40° C. for 3 months or no more than 1.88% dimers after storage at 25° C. for 6 months.

2. The formulation of claim 1 further comprising arginine.

3. The formulation of claim 2, wherein the arginine concentration is 50 to 300 mM.

4. The formulation of claim 1 further comprising methionine.

5. The formulation of claim 4, wherein the methionine concentration is 10 to 50 mM.

6. The formulation of claim 1 wherein the surfactant is polysorbate 80.

* * * * *